United States Patent [19]
Good et al.

[11] Patent Number: 5,646,351
[45] Date of Patent: Jul. 8, 1997

[54] ULTRASONIC MATERIAL HARDNESS DEPTH MEASUREMENT

[75] Inventors: Morris S. Good, Richland; George J. Schuster; James R. Skorpik, both of Kennewick, all of Wash.

[73] Assignee: Battelle Memorial Institute, Richland, Wash.

[21] Appl. No.: 529,847

[22] Filed: Sep. 18, 1995

Related U.S. Application Data

[63] Continuation-in-part of Ser. No. 309,363, Sep. 20, 1994, abandoned.

[51] Int. Cl.$^6$ .................................................. G01N 29/26
[52] U.S. Cl. ..................... 73/622; 73/597; 73/602; 73/631; 73/637; 73/644; 364/563
[58] Field of Search ......................... 73/622, 797, 637, 73/640, 600, 602, 618, 620, 644, 631; 364/551.01, 563, 487

[56]     References Cited

U.S. PATENT DOCUMENTS

| | | | |
|---|---|---|---|
| 3,169,393 | 2/1965 | Stebbins | 73/622 |
| 3,289,468 | 12/1966 | Van Der Veer et al. | 73/644 |
| 3,552,190 | 1/1971 | LeFebvre | 73/622 |
| 4,487,072 | 12/1984 | Livingston | 73/622 |
| 5,497,661 | 3/1996 | Stripf et al. | 73/611 |

FOREIGN PATENT DOCUMENTS 2105466  5/1983  United Kingdom ............... 73/622

OTHER PUBLICATIONS

Morris Good, "Effective Case Depth Measurement by an Ultrasonic Backscatter Technique", Sep. 1984, pp. 1–6.

*Primary Examiner*—Hezron E. Williams
*Assistant Examiner*—Nashmiya Ashraf
*Attorney, Agent, or Firm*—Paul W. Zimmerman

[57]     ABSTRACT

The invention is an ultrasonic surface hardness depth measurement apparatus and method permitting rapid determination of hardness depth of shafts, rods, tubes and other cylindrical parts. The apparatus of the invention has a part handler, sensor, ultrasonic electronics component, computer, computer instruction sets, and may include a display screen. The part handler has a vessel filled with a couplant, and a part rotator for rotating a cylindrical metal part with respect to the sensor. The part handler further has a surface follower upon which the sensor is mounted, thereby maintaining a constant distance between the sensor and the exterior surface of the cylindrical metal part. The sensor is mounted so that a front surface of the sensor is within the vessel with couplant between the front surface of the sensor and the part.

9 Claims, 5 Drawing Sheets

ULTRASONIC MATERIAL HARDNESS DEPTH MEASUREMENT

This invention was made with Government support under Contract DE-AC06-76RLO 1830 awarded by the U.S. Department of Energy. The Government has certain rights in the invention.

This application is a continuation-in-part of application Ser. No. 08/309,363 filed Sep. 20, 1994, now abandoned.

FIELD OF THE INVENTION

The present invention relates generally to a method and apparatus for detecting changes in material micro-structure or for identifying regions of a particular microstructure within a part. More specifically, the invention is an ultrasonic method and apparatus for measuring metal hardness depth.

BACKGROUND OF THE INVENTION

Measurement of hardness depth of metals has been previously reported by the American Society for Metals, Metals/Materials Technology Series 8408-003, EFFECTIVE CASE DEPTH MEASUREMENT BY AN ULTRASONIC BACKSCATTER TECHNIQUE, Morris S. Good, 15–20 Sep. 1984, herein incorporated by reference.

This paper reported use of an ultrasonic shear wave technique wherein the ultrasonic transducer was inclined at an angle of 18 degrees from a specimen orthogonal cross sectional plane. The transducer was 13 mm in diameter and had a 5.1 cm focal length, and a frequency of 10 MHz. Signals were generated and received through an ultrasonic pulser/receiver. Received signals passed through an amplifier to a waveform digitizer and averager, then to a CRT display. The CRT display was photographed and measurements of hardness depth taken from the photographs.

The specimen was rotated and 256 signals were obtained around the periphery of the specimen. Signal envelopes were averaged in the waveform digitizer and averager, thereby providing a stable and consistent envelope profile. The averaged envelope profile was used to determine onset of backscatter from the core grain structure. This envelope averaging was compared to metallurgically measured effective hardness depth and found to have a linear relationship therewith. It was reported, however, that the slope of the linear relationship of backscatter arrival time versus Rc 60 effective case depth deviates from the theoretical by as much as 45%.

The paper, specifically FIGS. 5B and 5C showing A-scans or amplitude scans, indicates a distortion of the signal envelopes. Ideally, the radio frequency (RF) signal received from the transducer and converted to a video signal amplitude should produce a smooth, well resolved envelope of the rectified RF signal. Instead, the video signal produced sharp peaks. Averages of signals having sharp peaks produced an envelope (FIG. 5C) having a rough signal with a jittery profile. In addition, the low amplitude signals in the RF signal are shown as a flat zero line in the video signal, thereby creating an artificial filter that rejects low amplitude signals. The envelope roughness, together with low amplitude signal rejection, reduces the accuracy of a threshold determination for the video signal. Loss of resolution of the envelope peak reduces the accuracy of the slope of the signal line between the low amplitude signals and the peak. Because it is this signal line and its slope that are used in determining hardness depth, it is desirable to obtain a line as accurate as possible.

Another source of surface hardness depth measurement error is seen in the paper in FIGS. 7B and 7C, wherein FIG. 7B the peak is about 4 scale units, and in FIG. 7C the peak is about 5 scale units. In the extreme, the peaks from part to part may be so disparate that it would be very difficult, if not impossible, to set a threshold limit. It is important that a hardness depth measurement system or procedure result in correct determination of hardness depth even when there is a high part to part amplitude variation.

Moreover, the fixture used and shown in FIG. 4 of the paper is rigid and does not account for part surface variation, for example eccentric surface variations. Because variations in surface geometry directly affect the determination of hardness depth, inaccurate measurements would result from a system that does not consider those variations.

Although not stated in the article, the envelope averaging was accomplished with electronic hardware, specifically an A/D converter made by Tektronix, Beaverton, Oregon, and the overall measurement procedure was quite slow, requiring from about 1 to about 3 minutes to obtain the 256 scans around the periphery of the specimen and significant additional time to subsequently determine hardness depth.

The slow measurement procedure coupled with the inaccuracies discussed above, must be overcome in order for such a system to be implemented in a commercial production facility.

SUMMARY OF THE INVENTION

The invention is an ultrasonic surface hardness depth measurement apparatus and method. The apparatus of the invention has a part handler, sensor, ultrasonic electronics component, computer, computer instruction sets, and may include a display screen.

The part handler has a vessel filled with a couplant, and a part rotator for rotating a cylindrical metal part with respect to the sensor. The part handler further has a surface follower upon which the sensor is mounted, thereby maintaining a constant distance between the sensor and the exterior surface of the cylindrical metal part. The sensor is mounted so that a front surface of the sensor is within the vessel with couplant between the front surface of the sensor and the part.

The sensor is a focused ultrasonic transducer having low side lobe interference.

The ultrasonic electronics component is located near the sensor, and sends and receives signals to and from the sensor. A gain control ensures that all signal peaks are about the same height from part to part.

In a preferred embodiment, the computer has a central processing unit, together with an A/D card and a control card. The A/D card rectifies the signal received as a waveform from the ultrasonic electronics component and smooths the signal profile, thereby enveloping the waveform, and subsequently averaging multiple envelopes to provide an averaged envelope. The control card controls the repetition rate of ultrasonic pulse generation. It will be apparent to one skilled in the art of ultrasonic electronic signal processing that the A/D card and control card may be placed within the ultrasonic electronics component or all cards and elements arranged in various groupings. Moreover, rectification, averaging, and repetition rate control may be accomplished with a variety of electronic elements beyond those shown and described herein.

The instruction sets are software programs or routines within the central processing unit for operator interface, data acquisition, data storage and data analysis. Data analysis is used for determining a hardness depth from the averaged envelope.

The display screen is optional, but can be used to visually display the averaged envelope and receive instructions from an operator.

A preferred method of the present invention for ultrasonically measuring hardness depth in a cylindrical metal part has seven main steps: (1) immersing the part in a couplant, (2) rotating the part with respect to a sensor, (3) sending ultrasonic waves from the sensor to the part and receiving scattered and/or reflected ultrasonic waves from the part, (4) converting received ultrasonic waves to electronic waveforms, preferably voltage amplitudes, (5) passing electronic waveforms to a computer wherein the electronic waveforms are rectified, gain controlled, smoothed and enveloped, (6) averaging a selected number of envelopes, and (7) determining an average hardness depth from the averaged envelopes. Optionally, the averaged envelope or other information may be shown on a display screen.

It is an object of the present invention to provide a method and apparatus for ultrasonic measurement of hardness depth in metal having improved accuracy, objectivity and speed.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1A:
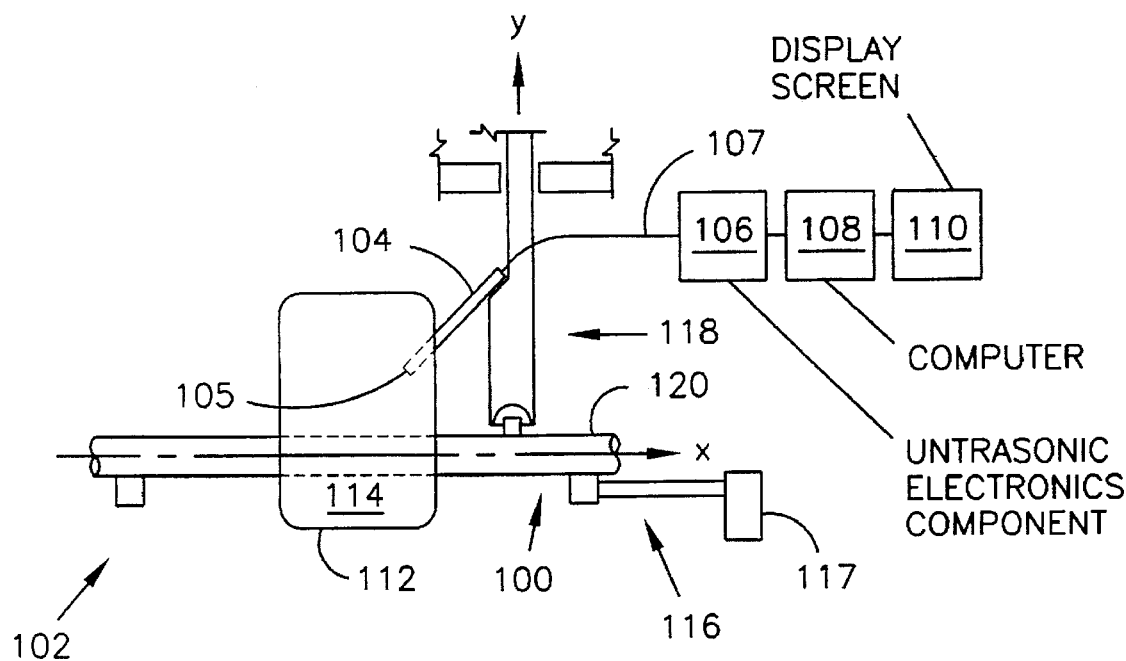
FIG. 1a is schematic of a first embodiment of an ultrasonic surface hardness measurement apparatus according to the present invention.
Figure 1B:
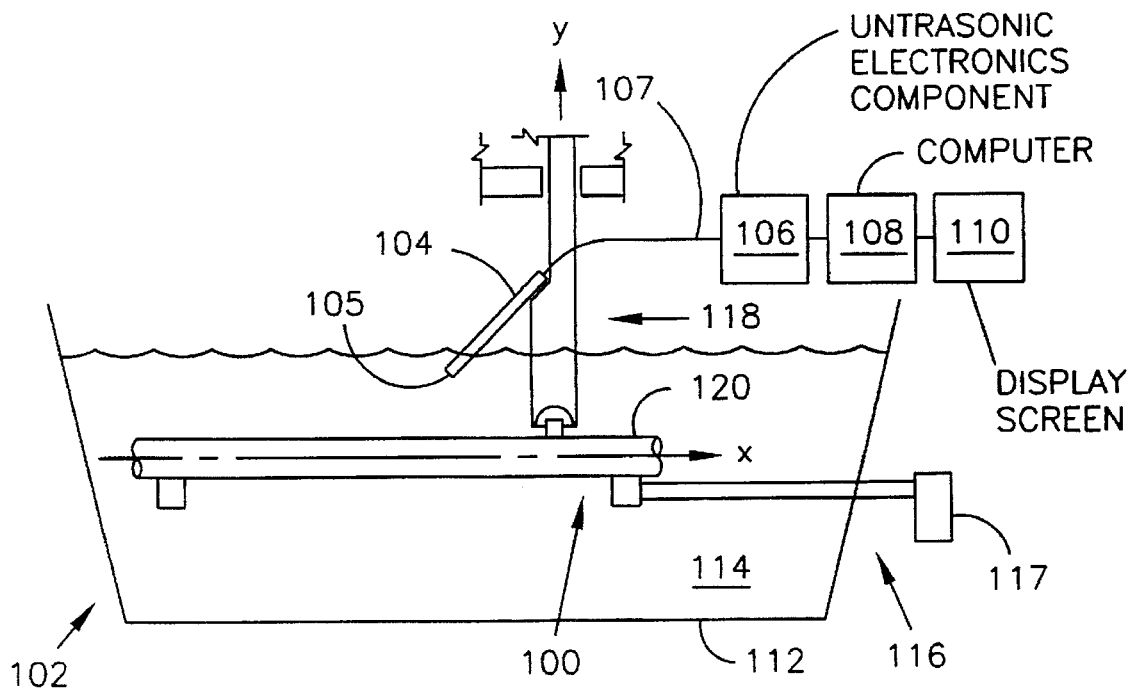
FIG. 1b is schematic of a second embodiment of an ultrasonic surface hardness measurement apparatus according to the present invention.

Referring to FIGS. 1a and 1b, there is shown an apparatus for ultrasonically measuring hardness depth in a cylindrical metal part 100. The apparatus has a part handler 102, sensor 104 having a front surface 105, ultrasonic electronics component 106, and a computer 108. Optionally, the apparatus may include a display screen The part handler 102 includes an immersion tank 112 filled with a couplant 114, and includes a part rotator 116 for rotating the cylindrical metal part 100 with respect to the sensor 104. The part rotator 116 includes a motor 117. The motor 117 may be unsubmerged in couplant as shown, or submerged in a sealed case (not shown).

As illustrated in FIG. 1a, the immersion tank may encompass only a portion of the part 100 or, as shown in FIG. 1b, encompass most or all of the part 100. The part handler 102 further has a surface follower 118 upon which is mounted the sensor 104 for maintaining a constant distance and orientation between the front surface 105 and the exterior surface 120 of the cylindrical metal part In a preferred embodiment as shown in FIG. 1b, the front surface 105 of the sensor 104, and the surface follower 118 are immersed in the couplant 114.

The sensor 104 is preferably a focused high frequency transducer with low side lobe interference. Frequency of the transducer is based upon (a) maintaining a factor of two or more difference in backscatter amplitude of hardened and unhardened metal, and (b) maintaining resolution between front surface and transition zone responses. Detection of unhardened core metal requires a high frequency ultrasonic signal. However, too high a frequency will cause too much backscatter from the hardened metal. Lower frequencies are desired when measuring deeper transition zones. However, too low a frequency results in no or insufficient backscatter from the unhardened metal and can result in decreased resolution between the front surface and transition zone responses. It is preferred, therefore, that transducer frequency be between about 5 MHz and about 50 MHz and more preferably from about 10 MHz to about 20 MHz.

The ultrasonic electronics component 106 is connected to the sensor 104 for sending and receiving signals to and from said sensor with minimum interference and noise. It is preferred that the connecting cable 107 be sufficiently short to avoid external interferences and/or internal electrical ringing. The ultrasonic electronics component 106 may be unsubmerged or partially immersed as shown or fully submerged in the couplant 114 and is preferably mounted upon the surface follower 118.

The computer 108 has a central processing unit together with an A/D card and a control card, wherein the A/D card rectifies the signal received as a waveform from the ultrasonic electronics component 106. The A/D card further envelopes the waveform, and subsequently averages multiple envelopes to provide an averaged envelope. The control card controls a repetition rate of ultrasonic pulse generation.

An instruction set within the central processing unit determines a hardness depth from the averaged envelope.

The surface follower 118 is shown in further detail in FIGS. 2a, 2b, 2c, and 2d. The purpose of the surface follower is to maintain a constant distance d (See FIG. 2a) between the sensor 104 and the part 100. It is also a purpose of the surface follower 118 to maintain a constant planar angle of incidence of emitted ultrasonic waves to a surface tangent of the part 100. The constant planar angle is accomplished by fixing a mount angle A as determined from a longitudinal sensor axis 201 and a vertical axis y. The sensor 104 is preferably mounted with the sensor axis 201 in a plane through a longitudinal axis x of the part 100, and with the sensor inclined at an angle from the vertical. The angle may be from about 8 degrees to about 27 degrees and is preferably about 18 degrees. Mounting the sensor 104 in this manner avoids or minimizes spurious acoustic reflections from projecting surfaces of the surface follower 118 and the part 100.

The surface follower 118 (see FIG. 2b) has three main elements, (a) a body 202 having a bottom 203 and a top 204, and at least one side surface 206, (b) at least one part contact 208 mounted on the body 202 near the bottom 203, and (c) at least one bearing 210 for providing at least one degree of freedom of motion of the surface follower 118. The part contact 208 may be a surface for sliding on the part 100, but is preferably a roller. Use of at least one roller is preferred to minimize the amount of frictional resistance between the surface follower 118 and the part 100 and/or the amount of marring of the part 100 produced as a result of the interaction between the part 100 and the part contact 208.

Figure 2A:
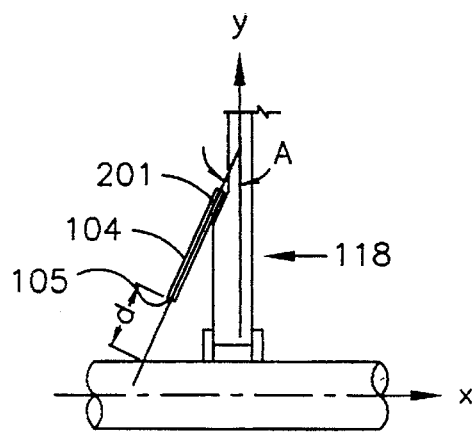
FIG. 2a is a schematic of a surface follower showing the relationship of the mounted sensor to the part.
Figure 2B:
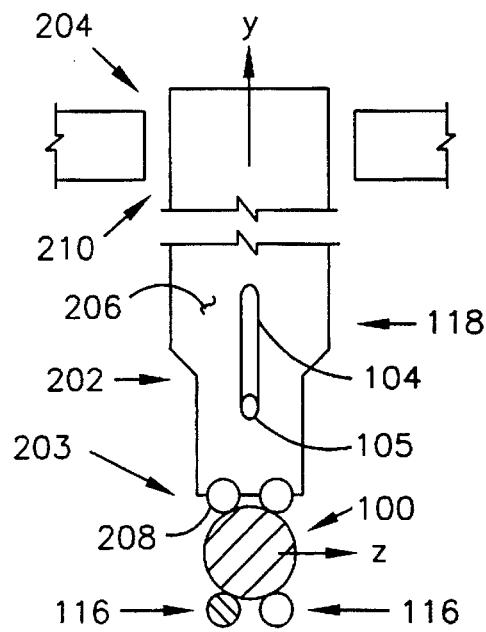
FIG. 2b shows a front view of one embodiment of a surface follower.
Figure 2C:
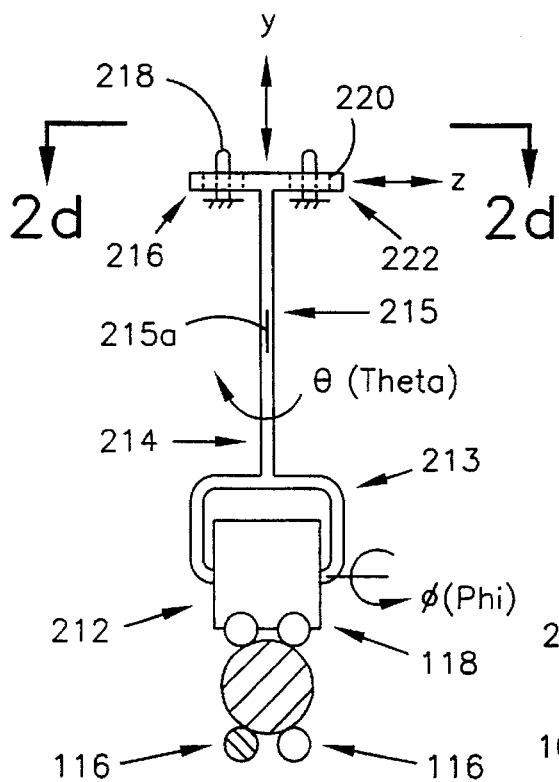
FIG. 2c shows a second embodiment of a surface follower.
Figure 2D:
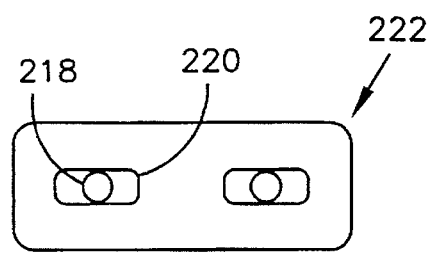
FIG. 2d is a detail of a surface follower bearing providing two translational degrees of freedom.

Because the part 100 may have geometric variations in straightness or surface trueness, and because it is desired that the surface contact 208 remain in contact with the part 100 during operation, it is preferred that the surface follower 118 be provided at least one degree of freedom of motion. Motion along the vertical axis y is permitted (See FIG. 2b) with a bearing 210. Additional degrees of freedom may be added as shown in FIG. 2c. Specifically, a bearing 212 and yoke 213 may be used permitting rotation phi about an axis parallel to the horizontal axis z. Further, a bearing 214 between the yoke 213 and a T-bar 215 permits rotation theta of the surface follower 118 about the vertical axis y. It is preferred that bearing 214 contain a pin 215a connecting the yoke 213 and the T-bar 215. Finally, a bearing 216 permits translation along the vertical axis y and the horizontal axis z. A preferred embodiment of the bearing 216 is shown in FIGS. 2c and 2d. At least one pin 218 that is fixed passes through a slot 220 through bracket 222. It will be apparent to those skilled in the art of mechanical bearings that other bearing types and arrangements may be used to obtain the desired degrees of freedom of motion of the surface follower 118.

Figure 2E:
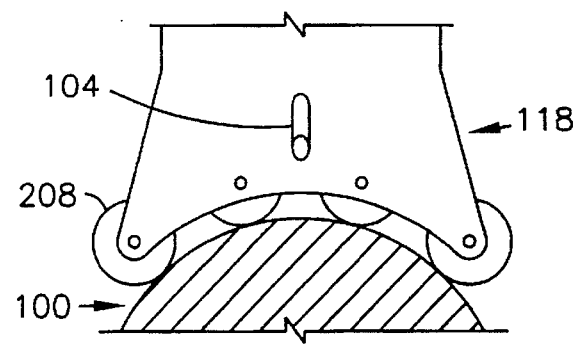
FIG. 2e shows a third embodiment of a surface follower for large diameter parts.

In a preferred embodiment, the surface follower 118 is adjustable to accept parts 100 of various diameters. Most preferably, the surface follower 118 is adjustable for accepting parts 100 ranging in diameter from about 1 cm to about 8 or 9 cm. It is further preferred that the apparatus accept parts 100 having lengths from about 3 cm to about 80 cm. FIG. 2e shows a surface follower 118 having rollers as the part contact 208 that may be used for larger diameter parts 100.

It is to be noted that motion along the horizontal axis x or the longitudinal axis of the part 100 is constrained. In other words, a bearing is not provided permitting free motion of the surface follower 118 along the horizontal axis x. It is preferred that the longitudinal position of the hardness depth measurement be precisely known. Thus, means for operator control of the position of the sensor 104 and surface follower 118 may be provided for making multiple measurements on a single part 100, but free motion along the horizontal axis x is constrained.

The speed of rotation of the part 100 is limited ultimately by the speed of sound of the series combination of the coupler 114 and the part 100. The rotation speed is further limited by vibration induced by an eccentricity of part 100. Rotational speed is also limited by the speed of data reduction in order to provide real time measurements. It is preferred to rotate the part well below any potential vibration problem and within the data processing and analysis time, since the amount of time that the part 100 is in the couplant 114 is small compared to the overall time of placement and retrieval. Hence, it has been found that rotational speeds of from below about 1 rpm to about 140 rpm and above are reasonable. In a preferred embodiment, speeds range from about 4 rpm to about 60 rpm. The most accurate hardness depth measurements are obtained when physical displacement bias, due to eccentricity of the part 100, is eliminated. The bias is eliminated by matching the time for one complete rotation with the time for obtaining an averaged envelope. Alternatively, different speeds may be used so that a correction factor of 1/n is used, wherein is the number of rotations per averaged envelope. If it is desired to measure variation or profile of hardness depth around the circumference of the part 100, then slower rotational speeds are preferred.

The relative spacing and alignment between the surface follower 118 and the part 100 is important to the present invention. A high tolerance of, at most, 0.1 mm is required, and a high tolerance of 0.02 mm is preferred. This equates to 0.06 mm (or 0.012 mm) high tolerance of the distance "d" because of the wave speed difference in the liquid couplant 114 (water) and the part 100 (steel). The usual method of correction of distance for ultrasonic measurements is by a zero (0) degree incidence signal that provides a stable signal. It is necessary for hardness depth measurement that the signal be inclined at an angle, thereby precluding the use of a zero degree incidence signal. The inclined or oblique angle of the signal causes front surface reflections to be sufficiently unstable that monitoring relative position in this manner would not permit accurate determination of hardness depth. Although a zero degree incidence signal could be added to the present invention, it is preferred to exclude a zero degree incidence signal and rely upon the tolerance of 0.06 mm achieved in the present invention with the part 100 having a high diametral tolerance and the rollers and bearings of the surface follower 118 having high mechanical tolerance.

Figure 3:
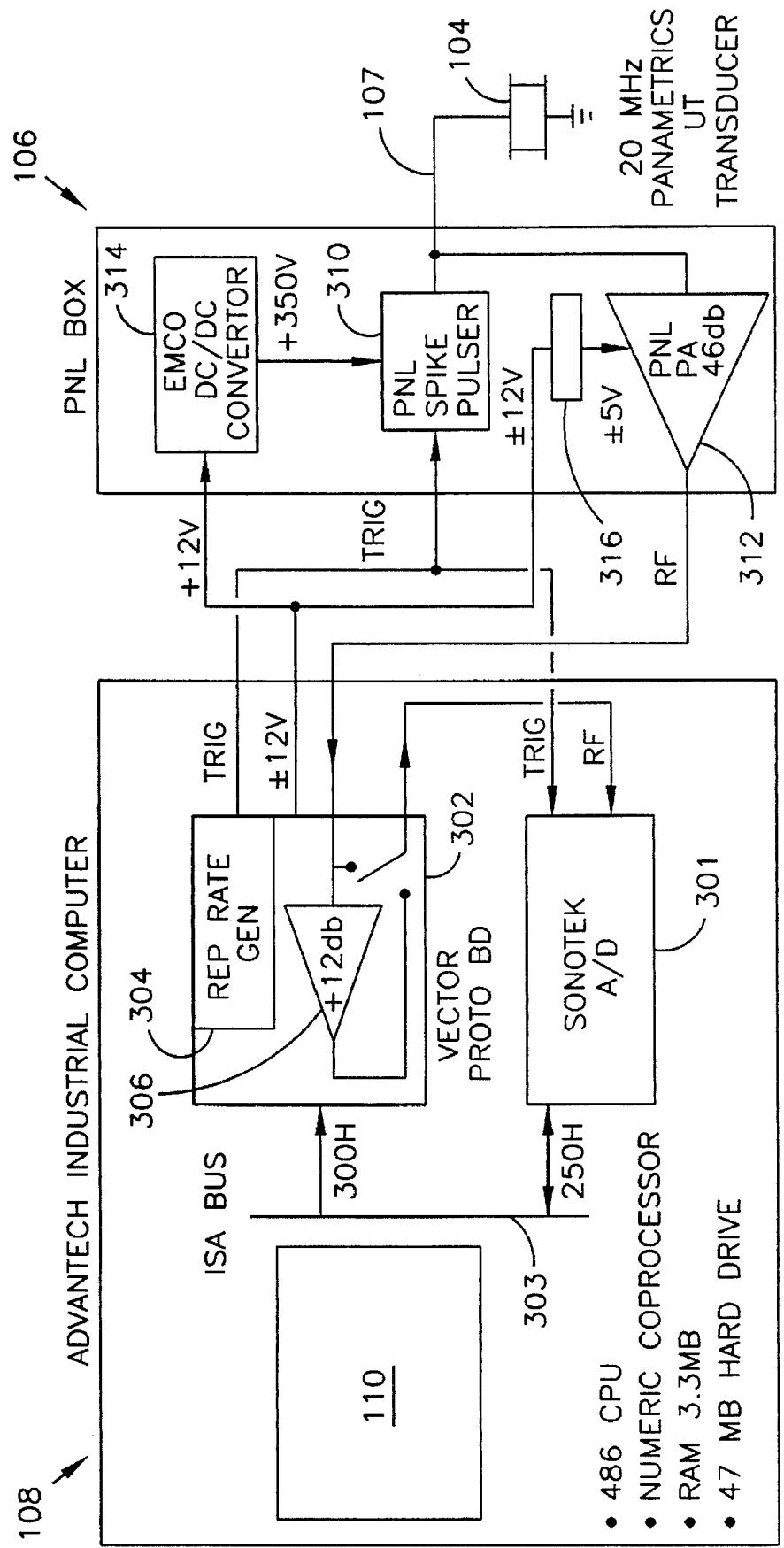
FIG. 3 is an electrical schematic of the electronic components of the ultrasonic surface hardness measurement apparatus.

A block diagram electronic schematic is shown in FIG. 3. In a preferred embodiment, the computer 108 has a central processing unit (not shown) together with an A/D card 301 and a control card 302, both connected to the computer bus 303. Although preferred, it is not necessary that either the A/D card 301 or the control card, or both, be combined with the computer 108. Either or both may be placed in the ultrasonic electronics component 106. Conversely, all of the ultrasonic electronics component 108 may be placed within the computer 108, together with the A/D card 301 and the control card 302.

The computer 108 is preferably a micro-computer that is compatible with personal computers. Further, it is preferred that the computer is industrial hardened. Features of industrial hardening include, but are not limited to, sealed front panel and switches, covered door floppy disc drive, and screen function keys.

The A/D card 301 rectifies the signal received as a waveform from the ultrasonic electronics component 106. The A/D card 301 further envelopes the waveform, and subsequently averages multiple envelopes to provide an averaged envelope. A preferred A/D card 301 is an STR, *8100 manufactured by General Research. This particular A/D card permits selective video filtering. For parts 100 having a shallow case depth and a rough surface finish, quick recovery from front surface reflection is necessary, and no filtering is done. For other parts 100 having deep hardness depths and/or smooth surfaces wherein recovery from front surface reflections is not needed, increased sensitivity is important and filtering is recommended. The STR*8100 permits selective filtering.

The control card 302 controls a repetition rate generator 304 producing ultrasonic pulses. Also, on the control card 302 is a variable gain amplifier 306.

The ultrasonic electronics component 106 contains a high voltage, high frequency pulser 310, having a fast rise time. The voltage may range from about 100 V to about 1000 V but is preferably from about 300 V to about 350 V. In addition, an amplifier 311 is used for received ultrasonic waves. The amplifier 311 may range from about 40 db to about 65 db, but is preferably from about 46 db to about 58 db. Voltage converters 314 and 316 are provided for the pulser 1O and the amplifier 312, respectively, for converting standard input voltage to pulser and amplifier operating voltages.

Figure 4:
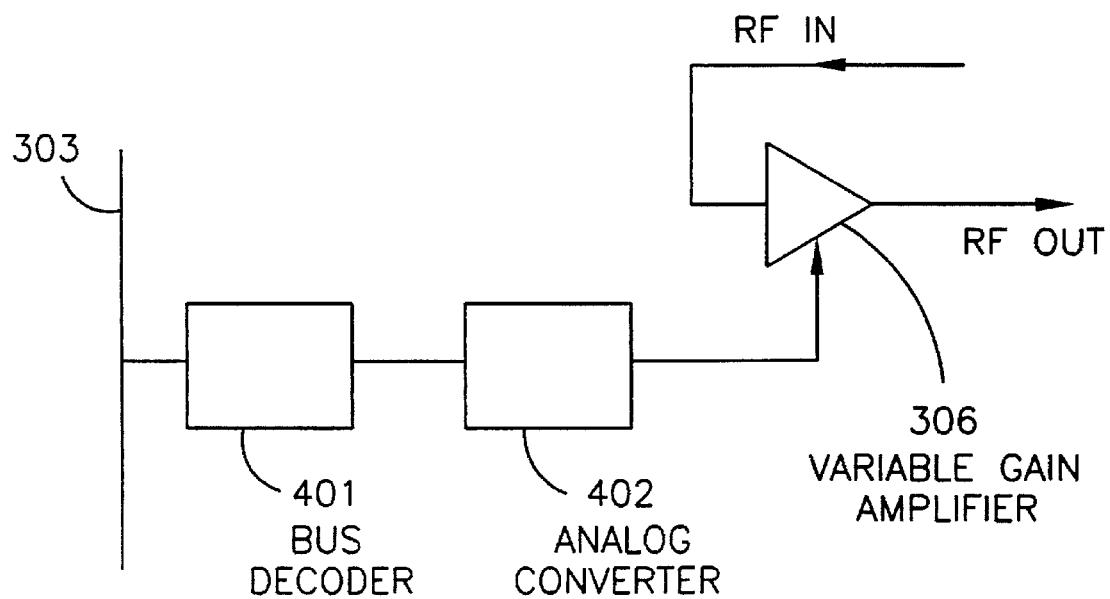
FIG. 4 is an electrical schematic of the gain control.

The variable gain amplifier 306 is connected to the computer bus 383 as shown in FIG. 4. The computer bus 303 is connected to a bus decoder 401 and a digital to analog converter 402, and thence to the amplifier 306.

During the course of operation of the apparatus in the absence of the variable gain amplifier 306, it was found that there was large variation in the signal amplitude from measurement to measurement especially from part to part for parts expected to have the same hardness depth. The response ultrasonic signal or ultrasonic response is a result of numerous scattering points wherein a response from each microstructural feature or scattering point combines to create an interference pattern that is unique for a particular circumferential or axial spatial location on the part 100. The response signals from each circumferential location are individually enveloped; then the envelopes are combined by averaging into a robust composite profile for an axial position. Gain control is then applied to the robust composite profile. Because of the high variability from envelope to envelope, accurate hardness depth is not obtainable by gain controlling individual envelopes.

This presented a problem inasmuch as low amplitude signals in one measurement were occasionally nearly as large as or larger than high amplitude signals in another measurement. When this occurred, the apparatus was unable to process the data. Hence, the control card 302 was provided with a gain control which gave additional capability to scale all signals so that the peak amplitudes had the same height from measurement to measurement. This gain control permitted measurements and data processing of parts independent of which hardening unit they came from and independent of other component variations and surface variations. The variable gain amplifier 306 may have an amplification range of up to 60-dB as represented by a lower limit of from about −10 to about 0 dB and an upper limit of from about 50 to about 60 dB. Within the 60 dB range, there are increments of amplification of about 2 or 3 dB. In a preferred embodiment, the variable gain amplifier 306 has an amplification range of about 12 dB with a lower limit of 0 dB and an upper limit of 12 dB.

The computer 108 contains instruction sets or software for four basic operations, (1) operator interface, (2) data acquisition, (3) data storage, and (4) data analysis. The data analysis is the determination of hardness depth from the averaged, envelope. Data acquisition includes control of the gain of the variable gain amplifier 306, controlling repetition rate of the repetition rate generator 304, calibration, and set-up of the A/D card 302. Set-up of the A/D card includes post trigger delay for beginning a backscatter profile at a front surface of the part 100, voltage range selection for sensitivity adjustment, voltage offset to adjust a baseline of the backscatter profile and to fully utilize the A/D card 302 dynamic range, blanking threshold, detection threshold, envelope filter, selection of digitization rate, and number of points or length (depth) of the backscatter profile.

Figure 5:
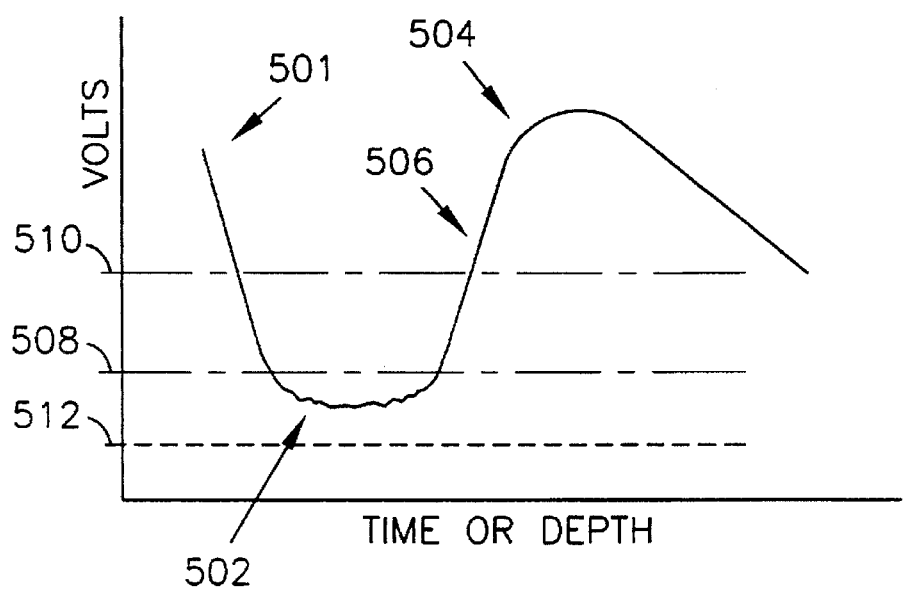
FIG. 5 is a graph of data obtained by the apparatus.

Blanking and detection thresholds are used to detect the transition between hard and soft steel. The back-scatter profile (see FIG. 5) has a large front surface response 501, a low amplitude plateau 502 of the hardened microstructure, and a middle range amplitude 504 which peaks, then decays exponentially. The transition 506 from the plateau 502 to the amplitude 504 is the desired feature for determining hardness depth. Minimization of false detection and increased reliability is achieved by use of a blanking threshold 508. The blanking threshold 508 blocks the surface response 501 until it is lower than the blanking threshold 508. A detection threshold 510 blocks the transition 506 until it exceeds the detection threshold 510. The gap or difference between the blanking threshold 508 and the detection threshold 510 minimizes a possibility of false detection from signal irregularities. The time value of the transition 516 at detection is provided to the computer for determination of hardness depth. A baseline 512 is established to reject signals or waves having amplitudes less than or equal to apparent signals present when the sensor 104 is at a practically infinite distance from the part 100.

Figure 5A:
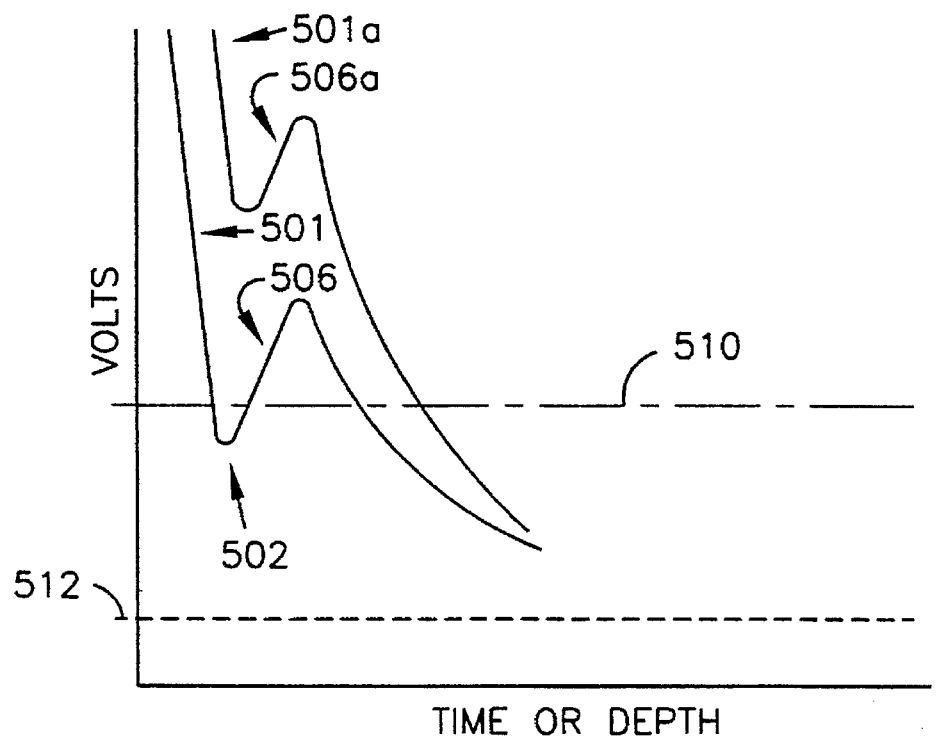
FIG. 5a is a graph of data for a hardness depth of 1.2 mm.

The amount of time between the surface response 501 and the transition 506 corresponds to the hardness depth. Hence, it is necessary that the transition 506 be distinguishable from the surface response 501. There is a trade-off between depth resolution and signal sensitivity. In general, better signal sensitivity results in reduced depth resolution. For example, for a part having a hardness depth of 1.2 mm and a slightly rough surface, filtering to obtain additional signal amplitude causes the filtered transition 506a and the filtered surface response 501a to be so close together as to nearly preclude detection of the transition 506a (FIG. 5a).

For a part having a hardness depth of 5.6 mm, much of the transition 506 (FIG. 5b) is below the detection threshold 510. Hence, greater signal sensitivity is needed. In this instance, filtering increases the observed transition 506b, but there is still sufficient distance or time between the filtered transition 506b and the filtered surface response 501b that adequate depth resolution is maintained.

Figure 5B:
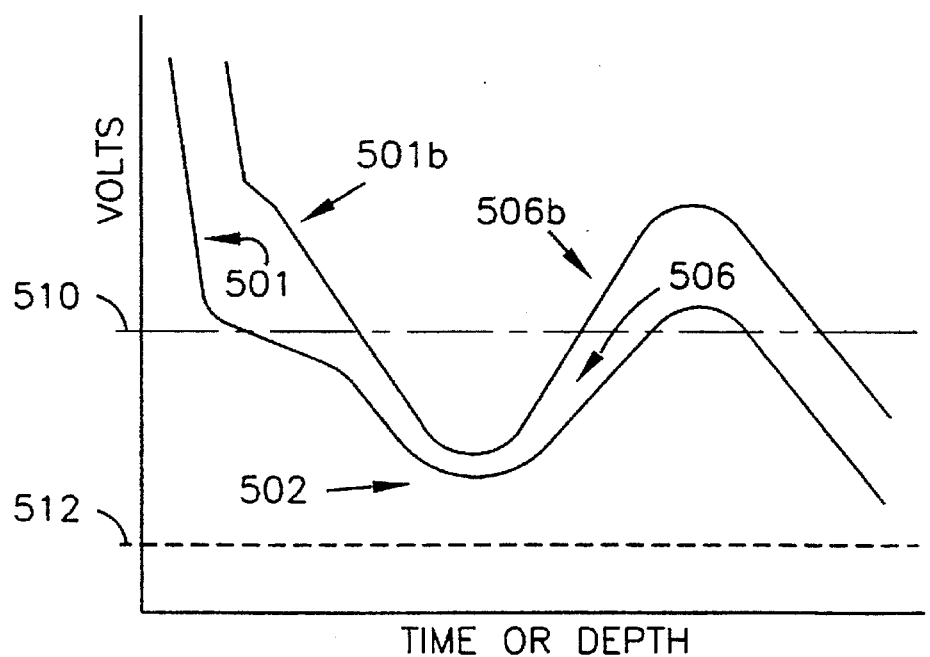
FIG. 5b is a graph of data for a hardness depth of 5.6 mm.

In general, it is understood by those of skill in the art of electric signal filtering that filtering usually broadens peaks and reduces amplitudes of peaks. However, in our application, we were surprised that the STR,88100-D card actually increased signal amplitude upon filtering as shown in FIGS. 5a and 5b.

Calibration is used to set slope and intercept values of a linear relationship between the time value of the transition and the hardness depth. The algorithm relies upon the distance d between the sensor 104 and the part 100 for establishing the hardness depth. Although it is possible to ultrasonically obtain a part surface 120 location and an identification of hardness transition within the part 100, it is preferred to make the distance to the part surface 120 a constant with the surface follower 118 so that only one variable, namely hardness transition, need be determined ultrasonically. The ultrasonic signal from the part surface 120 is unstable or inconsistent. Instability results from irregularities and/or roughness of the part surface 120. Thus, determination of hardness depth from a difference of two ultrasonically determined variables would introduce much more measurement uncertainty than determination of hardness depth from a difference of a fixed sensor-to-part distance and the ultrasonically determined transition.

Another source of measurement uncertainty is the fact that the speed of sound in a material is dependent upon the temperature of the material. Hence, the couplant 114 is heated and maintained at a selected temperature, preferably 5 near the temperature of the received part 100. Because a greater mass of couplant 14 would experience a smaller temperature change than a lesser mass of couplant 14, it is presently preferred to use the apparatus of FIG. 1b because of the greater mass of couplant 14 compared to the apparatus of FIG. 1a.

EXAMPLE 1

An experiment was conducted to compare the surface hardness depth measurement as obtained by the present invention apparatus and method and as obtained by a standard destructive measurement.

The destructive test procedure was Rockwell hardness test set forth in the book, *Case Hardening of Steel*, ed. HE Boyer, 1987, ASM International, Meadows Park Ohio, pp 249–250. A Rockwell hardness tester manufactured by Wilson was used.

Sixteen hardened axles from three batches were received from General Motors. Samples 1 and 2 were arbitrarily selected as calibration samples. Each axle was subjected to both the ultrasonic apparatus and method of the present invention, as well as the destructive test method.

In these 16 samples (see Table 1), the average error of surface hardness depth for the ultrasonic test compared to the destructive test is about 2.4%.

TABLE 1

| | Ultrasonic and Destructive Hardness | |
| --- | --- | --- |
| Sample | Batch | Ultrasonic Hardness (mm)/ Error (mm) | Destructive Hardness (mm) |
| 1 | C | 3.2/0.0 | 3.2 |
| 2 | B | 5.6/0.0 | 5.6 |
| 3 | A | 4.2/–0.1 | 4.3 |
| 4 | B | 3.2/0.0 | 3.2 |
| 5 | A | 3.1/–0.1 | 3.2 |
| 6 | C | 3.6/–0.1 | 3.7 |
| 7 | A | 3.5/–0.2 | 3.7 |
| 8 | B | 4.1/–0.2 | 4.3 |
| 9 | C | 4.3/0.0 | 4.3 |
| 10 | C | 4.5/–0.1 | 4.6 |
| 11 | A | 4.5/–0.1 | 4.6 |
| 12 | A | 5.3/+0.3 | 5.0 |
| 13 | A | 5.3/+0.1 | 5.2 |
| 14 | B | 5.1/–0.1 | 5.2 |
| 15 | C | 5.7/+0.1 | 5.6 |
| 16 | B | 5.8/+0.2 | 5.6 |

EXAMPLE 2

An experiment was done to determine the presence of hardness run-out on either end of a steering linkage piston rod using the ultrasonic apparatus of the present invention.

In this experiment, seven sets of rods were hardened. Some were purposely hardened completely over their entire lengths, and some were hardened in the middle span of the rods, leaving either end or both ends in an unhardened condition for purposes of insertion into a press fit or tapping of threads.

Use of the ultrasonic apparatus and method resulted in confirming the presence or absence of an unhardened end. Unhardened end sections measured between about 0 to about 2 cm.

EXAMPLE 3

An experiment was conducted to quantify the length of weldable material on an end of a tube. The tube body is made of a non-weldable metal matrix composite that has a transition from the metal matrix composite to a weldable metal at one or both ends of the tube. Specifically, the tube was made of aluminum metal having 15% by weight silicon carbide in a metal matrix composite.

The ultrasonic apparatus and method of the present invention were modified for this experiment. Instead of obtaining an a-scan, a b-scan or brightness scan was obtained. Also, instead of obtaining measurements about the circumference of the tube, measurements were obtained along its length. The destructive test use for comparison was a sectioning, polishing and etching procedure commonly used for identification of silicon carbide particles.

The destructive test showed a substantially linear transition from the 15% by weight silicon carbide in aluminum non-weldable metal matrix composite to weldable aluminum metal over a length of about 2.5 cm.

The ultrasonic test showed a substantially linear transition from non-weldable metal matrix composite to weldable aluminum over a length of about 2.5 cm.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An apparatus for ultrasonically measuring hardness depth in a cylindrical metal part having an exterior surface, hardened zone and an unhardened core, said apparatus comprising:

(a) a part handler having a vessel filled with a couplant, and a part rotator for rotating the cylindrical metal part with respect to a sensor, said part rotator further having a surface follower upon which is mounted the sensor for maintaining a high tolerance fixed distance and non-perpendicular angular orientation between the sensor and the exterior surface, thereby excluding a zero incidence signal for determining said high tolerance fixed distance, and maintaining said couplant between the sensor and the part;

(b) said sensor having a frequency between about 5 MHZ and about 50 MHZ for maintaining a backscatter amplitude difference between said hardened zone and said unhardened core of at least a factor of two;

(c) an ultrasonic electronics component connected to the sensor for sending and receiving a plurality of signals to and from said sensor;

(d) a computer having a central processing unit;

(e) an A/D card that rectifies each of the plurality of signals, each signal received as a waveform from the ultrasonic electronics component, and smoothes a signal profile of the waveform, thereby enveloping the waveform, and subsequently averaging multiple envelopes of the plurality of waveforms to provide a robust composite profile, the A/D card further having a selective filter for setting profile filtering for obtaining a robust composite profile amplitude having a desired signal sensitivity and depth resolution;

(f) a control card for controlling a repetition rate of ultrasonic pulse generation, the control card further having a variable gain amplifier for scaling each of the plurality of waveforms from the A/D card so that each peak amplitude of the plurality of waveforms has a same height from measurement to measurement, thereby permitting measurements and data processing of parts independent of cylindrical metal part variations; and (g) an instruction set within the central processing unit for determining a hardness depth from the gain controlled robust composite profile.

2. The apparatus as recited in claim 1, wherein the surface follower comprises:

(a) a body having a bottom and a top, and at least one side surface;

(b) at least one roller rotatably mounted on said body near the bottom, said roller(s) contacting the part; and (c) at least one bearing providing at least one degree of freedom of motion, thereby maintaining the sensor at the high tolerance fixed distance from the exterior surface.

3. The apparatus as recited in claim 1, wherein the ultrasonic electronics component comprises:

(a) a pulser for sending signals to the sensor;

(b) an amplifier for receiving reflected signals from the sensor; and (c) a pulser voltage converter and an amplifier voltage converter for converting standard input voltage to pulser and amplifier operating voltages.

4. The apparatus as recited in claim 3, wherein the pulser operates at a voltage from about 100 V to about 1000 V.

5. The apparatus as recited in claim 3, wherein the pulser operates at a voltage from about 300 V to about 350 V.

6. A method for ultrasonically measuring hardness depth in a cylindrical metal part having an exterior surface, said method comprising the steps of:

(a) immersing a portion of the cylindrical metal part in a couplant;

(b) rotating the cylindrical metal part with respect to a sensor wherein the couplant is maintained between the sensor and the part, and said sensor is maintained a substantially constant high tolerance distance from the exterior surface and said sensor is at an oblique angle with respect to an axis of the cylindrical metal part;

(c) sending ultrasonic waves from said sensor through said couplant and into the cylindrical metal part and receiving reflected waves from within the cylindrical metal part and converting them to electronic waveforms;

(d) rectifying each of the waveforms and gain controlling each of the waveforms, so that each peak amplitude of each of the waveforms has a same height from measurement to measurement, and smoothing a signal profile of each of the waveforms, thereby enveloping each of the waveforms, and subsequently averaging multiple envelopes and providing a robust composite profile;

(e) selectively filtering the robust composite profile for obtaining a robust composite profile amplitude having a desired signal sensitivity and depth resolution;

(f) determining a hardness depth from the robust composite profile.

7. The method as recited in claim 6, wherein the sensor is maintained the substantially constant high tolerance distance from the exterior surface with a surface follower.

8. The method as recited in claim 7, wherein ultrasonic waves are produced with a pulser and the sensor.

9. The method as recited in claim 7, wherein the gain control is computer controlled.

* * * * *

UNITED STATES PATENT AND TRADEMARK OFFICE
CERTIFICATE OF CORRECTION

PATENT NO. : 5,646,351
DATED : 07/08/97
INVENTOR(S) : Good et al.

It is certified that error appears in the above-indentified patent and that said Letters Patent is hereby corrected as shown below:

In column 4, line 15, after the word "part", please insert the number --100.--.

In column 4, line 60, please replace "1OO" with --100.--.

In column 6, line 55, please replace "STR," with --STR--.

In column 7, line 5, please replace "311" with --312--.

In column 7, line 6, please replace "311" with --312--.

In column 7, line 9, please replace "1O" with --310--.

In column 7, line 13, please replace "383" with --303--.

In column 7, line 55, after the word "averaged", please omitt the comma.

In column 8, line 14, please replace "516" with --506--.

UNITED STATES PATENT AND TRADEMARK OFFICE
CERTIFICATE OF CORRECTION

PATENT NO. : 5,646,351
DATED : 07/08/97
INVENTOR(S) : Good et al.

It is certified that error appears in the above-indentified patent and that said Letters Patent is hereby corrected as shown below:

In column 8, line 42, please replace "STR, 88100-D" with --STR*88100-D--.

In column 9, line 1, please replace "14" with --114--.

In column 9, line 2, please replace "14" with --114--.

In column 9, line 4, please replace "14" with --114--.

In column 10, line 58, please replace the word "the" with the letter --a--.

Signed and Sealed this

Eleventh Day of November, 1997

Attest:

BRUCE LEHMAN

Attesting Officer

Commissioner of Patents and Trademarks